United States Patent [19]

Giaever

[11] 4,054,646
[45] Oct. 18, 1977

[54] METHOD AND APPARATUS FOR DETECTION OF ANTIBODIES AND ANTIGENS

[75] Inventor: Ivar Giaever, Schenectady, N.Y.

[73] Assignee: General Electric, Milwaukee, Wis.

[21] Appl. No.: 608,255

[22] Filed: Aug. 27, 1975

Related U.S. Application Data

[63] Continuation-in-part of Ser. No. 384,113, July 30, 1973, abandoned.

[51] Int. Cl.$^2$ .................... G01N 21/06; G01N 33/16
[52] U.S. Cl. ..................... 424/12; 23/230 B;
23/253 TP; 23/259; 128/2 R; 260/112 R;
427/250; 428/336; 428/434; 428/469; 428/474;
324/71 R; 324/158 R
[58] Field of Search ............ 23/230 B, 253 TP;
424/12, 85, 88; 260/112 R

[56] References Cited

U.S. PATENT DOCUMENTS

| | | | |
|---|---|---|---|
| 2,666,355 | 1/1954 | Trurnit | 356/108 |
| 3,171,783 | 3/1965 | Fisk | 424/12 |
| 3,236,732 | 2/1966 | Arquilla | 424/12 X |
| 3,313,706 | 4/1967 | Lembke | 424/12 X |
| 3,492,396 | 1/1970 | Dalton | 424/12 |
| 3,639,558 | 2/1972 | Csizmas | 424/12 |
| 3,639,559 | 2/1972 | Tax | 424/12 |
| 3,646,346 | 2/1972 | Catt | 424/12 X |
| 3,658,982 | 4/1972 | Reiss | 424/12 |
| 3,697,645 | 10/1972 | Meier | 424/85 |
| 3,733,398 | 5/1973 | Shulman | 424/12 |
| 3,770,380 | 11/1973 | Smith | 424/12 |
| 3,820,953 | 6/1974 | McEwan | 23/230 R |
| 3,926,546 | 12/1975 | Giaever | 204/192 P X |
| 3,979,184 | 9/1976 | Giaever | 23/230 B X |

FOREIGN PATENT DOCUMENTS

| | | |
|---|---|---|
| 1,228,698 | 4/1971 | United Kingdom |
| 1,248,764 | 10/1971 | United Kingdom |
| 1,248,765 | 10/1971 | United Kingdom |

OTHER PUBLICATIONS

I. Giaever, Jour. of Immunology, vol. 110, 1424–1426 (1973).
Press Release by General Electric, "Simplified Method of Blood Analyses Discovered by GE Scientist", issued Nov. 22, 1972.
A. Rothen et al., Helvetica Chimica Acta, 54, (Fasc. 4), 1208–1217, (1971).
Langmuir et al., J.A.C.S., vol. 59, 1406 (1937).
A. Rothen, Physiological Chem. & Physics, vol. 5, 243–258 (1973).
Vroman et al., Federation Proceedings, vol. 30, 1494–1502 (1971).

*Primary Examiner*—Sidney Marantz
*Attorney, Agent, or Firm*—Morgan, Finnegan, Pine, Foley & Lee

[57] ABSTRACT

Method and apparatus for the detection of antibodies and antigens based upon the effect that any arbitrary antigen will adsorb onto a substrate in a monomolecular layer only, but that a corresponding specific antibody for such arbitrary antigen will bond thereto to form a bimolecular layer on the substrate. A first layer of antigen is adsorbed onto a substrate and the coated substrate is then exposed to a solution suspected of containing the specific antibody of interest. The substrate is then examined to determine whether a monomolecular or bimolecular layer is adhering thereon. Optical, including visual, electrical, and chemical means for examining the coated substrate are disclosed. The method can be reversed by replacing the antigen in each step above with its specifically reacting antibody and by replacing the antibody with its specific antigen.

60 Claims, 13 Drawing Figures

METHOD AND APPARATUS FOR DETECTION OF ANTIBODIES AND ANTIGENS

CROSS-REFERENCE TO RELATED APPLICATION

This application is a continuation-in-part of Ser. No. 384,113 entitled "Improved Method and Apparatus for Detection and Purification of Proteins and Antibodies" and filed July 30, 1973, now abandoned.

FIELD OF THE INVENTION

This invention relates to an immunological test method and apparatus for detection of antibodies and antigens. More particularly, this invention relates to detection of such biological constituents where the antigen-antibody interaction takes place at the surface of a substrate.

BACKGROUND OF THE INVENTION

This application contains subject matter which is related to that in patent application Ser. No. 266,278 entitled "Method and Apparatus for Detection and Purification of Proteins and Antibodies" filed June 26, 1972, now abandoned; Ser. No. 392,950 entitled "Method For Binding Antibodies To a Surface Such That They Remain Active" filed Aug. 30, 1973 now abandoned; and Ser. No. 392,951 entitled "Method for Improving Contrast in Surface Immunological Tests with Large Size Proteins" filed Aug. 30, 1973, now abandoned all having a common applicant and assignee.

Other publicantions related to the present invention primarily as background are "Optical Measurement of the Thickness of a Film Adsorbed from a Solution", authors Irving Langmuir et al. Journal of the American Chemical Society, Vol. 59 (July-December 1937) page 1406; "Immunological and Enzymatic Reactions Carried Out at a Solid-Liquid Interface" by Alexandre Rothen, Physiological Chemistry and Physics, 5, (1973), pages 243-258; "Interactions Among Human Blood Proteins at Interfaces", Leo Vroman et al, Federation Proceedings, Vol. 30, No. 5 (September-October 1971) pages 1494-1502; and "The Antibody-Antigen Reaction: A Visual Observation", Ivar Giaever, The Journal of Immunology, Vol. 110, No. 4 (May 1973) pages 1424-1425.

Immunological reactions are highly specific interactions in which an antigen interacts with a corresponding second biological constituent specific to the antigen and generally known as the antibody to form an immunological complex. Immunological reactions taking place within a biological system such as an animal or a human being are vital in combating disease. In a biological system, the entry of a foreign biological constituent, e.g., the antigen, causes the biological system to produce the specific antibody to the antigen in a process not fully understood at this time. The antibody molecules have available chemical combining or binding sites which complement those on the antigen molecule so that the antigen and antibody combine or bond to form the immunological complex.

Antibodies are produced by biological systems in response to invasion thereof by foreign bodies. Consequently, the detection of antibodies present in a biological system is of medical diagnostic value in determining the antigens to which the system has been exposed. It would be useful, for example, to test for the presence of the antibody to syphilis or gonorrhea in human blood, plasma or tissue. Conversely, the detection of certain antigens in a biological system also has medical diagnostic values; examples of diagnostic detection of antigens include detection of human chorionic gonadotrophin (HCG) protein molecules in urine as a test for pregnancy, and detection of hepatitis-associated antigen (HAA) molecules in blood of prospective blood donors.

Most antigens are proteins or contain proteins as an essential part, whereas all antibodies are proteins. Proteins are large molecules of high molecular weight, i.e., are polymers consisting of chains of amino acids. The antigen and antibody protein may each have several combining sites. The five major classes of antibodies (immunoglobulins IgG, IgM, IgA, IgE and IgD are each apparently characterized by at least two heavy (long) peptide chains of amino acids and at least two light (short) peptide chains of the acids wherein the bond between the amino acids units is known as a peptide bond. These heavy and light peptide chains are oriented in the general shape of the letter "Y" and the active or combining sites are the extreme ends of the two arms of the Y-shaped antibody for the IgG antibody.

In addition to the immunological reaction which occurs between specific protein antigens and specific protein antibodies resulting in the formation of a protein antigen-protein antibody complex, other immunological complexing reactions between immunologically reactive antigens and antibodies are also contemplated by this invention. In addition, specific reactions between other biological particles, such as enzymes and their substrates, are also among the methods contemplated and are embraced by the term "immunological reaction" as used herein. Furthermore, as used herein, the terms "antigen" and "antibody" are meant to encompass such terms as enzymes, substrates, and similar biological particles. As will also be seen, the method is versatile enough to permit substitution of a specific antibody for the corresponding antigen and the antigen for the corresponding specific antibody.

For instance, the following systems include biological particles which are capable of undergoing the immunological reactions described herein:

Viruses
Bacteria and Bacterial toxins
Fungi
Parasites
Animal tissue
Animal body fluids, and the like.

With respect to viruses, the antigens are viral cultures, or parts thereof, and the antibody specific thereto can be produced by administration to a living host. Illustratively, antigen-antibody complexes in the following virus systems are useful in the hereindisclosed procedure: Rubella virus culture (antigen) — Rubella virus antibody; polio virus culture (antigen) — polio virus antibody; vesicular stomatitis virus (VSV) culture (antigen) — VSV antibody.

Regarding bacteria and bacterial toxins, the antigens are the particular bacteria or bacterial toxin, or parts thereof, and the antibody is produced by injection into a living host. The following are illustrative examples of antigen-antibody pairs which can be used in the present method: tetanus toxoid suspension (antigen) — tetanus antibody; diptheria toxin suspension (antigen) — diptheria antibody; Neisseria gonorrhoea suspension (antigen) — gonorrhea antibody; Treponema palladium suspension (antigen) — syphilis antibody.

As for fungi, the antigens are antigenic extracts of fungal suspensions and the antibody is the fungal antibody produced by injection into a living host. Antigen-antibody complexes of fungi systems are illustrated by the following: Aspergillus extract suspension (antigen) — aspergillus fungus antibody; Candida extract suspension (antigen) — candida fungus antibody.

Antigens and antibodies in parasite systems are tested in a similar fashion to those of fungi. The system Toxoplasma gondii extract (antigen) — Toxoplasma gondii antibody is a typical example.

By the term polysaccharides is meant a system wherein the antigen is a carbohydrate antigen. An example of such an antigen-antibody containing system is pneumococcus polysaccharides (antigen) — pneumococcus antibody.

In addition to the typical enzyme-enzyme substrate reaction which is intended to be covered herein, enzymes themselves, or parts thereof, may be utilized as antigens, and the antibody is the particular enzyme antibody elaborated by a living host after injection. Illustrative antigen-antibody complexes of enzyme systems are:

trypsin extract — trypsin antibody
chymotrypsin extract — chymotrypsin antibody
pepsin extract — pepsin antibody
ribonuclease extract — ribonuclease antibody
thrombin extract — thrombin antibody
amylase extract — amylase antibody
penicillinase extract — penicillinase antibody With respect to hormones, the antigenic constituent is usually found in a hormone extract and the antibody is the particular hormone antibody elaborated by the living organism after injection. An exemplary antigen-antibody complex is:

insulin — insulin antibody.

Although the ensuing discussion is directed for the most part to immunological interactions between specific protein antigens and specific protein antibodies, it is understood that it also applied to the systems and the immunologically reactive antigens and antibodies hereinabove described.

As presently practiced, the diagnostic utilization of immunologically active antibodies and antigens relay upon the precipitating or agglutinating characteristic thereof resulting from the immunological complexing reaction. The classic example of these diagnostic uses is the blood typing procedure in which blood samples are mixed with alpha and beta type serum antibodies and blood type is determined by observing any agglutination occurring in the blood samples.

The HCG pregnancy test as currently practiced is an inhibition test. The test is performed by mixing a quantity of HCG anti-serum into a urine specimen. A plurality of polystyrene spheres which have been coated with HCG protein are then introduced into the previously prepared urine specimen. The polystyrene spheres will agglutinate if, but only if, HCG protein is absent from the urine specimen. If HCG protein is absent from a urine specimen, the HCG protein on the polystyrene spheres complexes with the HCG anti-serum previously introduced in the urine specimen and the spheres agglutinate. If, on the other hand, HCG protein is present in sufficient quantities in the urine specimen, it complexes with the previously introduced HCG anti-serum forming a complex which precipitates out of the specimen so that the previously introduced anti-serum is no longer available to complex with the HCG protein on the spheres to cause agglutination thereof. In accordance with the teachings of this disclosure, the present HCG protein pregnancy test could be simplified by adhering HCG anti-serum onto the polystyrene spheres and directly testing a urine specimen. In this case, the polystyrene's spheres would agglutinate if, but only if, HCG protein is present in the specimen.

It appears that the reason this simpler procedure has not been employed is that the available HCG anti-sera are complex mixtures containing a large proportion of constituents other than HCG antibodies. The additional effort required in the prior art to extract the antibodies from the HCG anti-sera make the inhibition test, utilizing sera directly, preferable in the prior art. However, in accordance with one embodiment of this invention, a procedure is provided whereby the simpler, direct test is performable. A serious shortcoming of agglutination tests overcome by the present direct method is that the particles involved may tend to agglomerate for any of a variety of reasons having nothing to do with immunological agglutination thereby decreasing the reliability of the test. Typically, even though agglutination tests are performed with great care by skilled technicians, nevertheless occasional diagnostic errors occur.

Even though it is known that the antibody-antigen complexing reaction will take place when an antigen (or antibody) is adsorbed at a surface, the technique has not been widely applied to routine medical diagnoses on slide like substrates. The complexing reaction at a surface has been observed by means of an ellipsometer. An ellipsometer is a complex optical instrument by means of which it is possible to measure the thicknesses of films on the order of 0.1 A. Ellipsometers are expensive and require skilled operators. In studies of immunological reactions using ellipsometers performed to date, two methods have been used. In one method, the reaction to be studied is allowed to take place and then the slide on which the reaction has taken place is mounted in an ellipsometer and an actual measurement of film thickness is made. In the other method, the slide is mounted in the ellipsometer while the immunological reaction is taking place and the change of film thickness is observed with the ellipsometer. The measurement of absolute thickness requires extreme care. On the other hand, when the concentration of antibodies in the solution is low, the measurement of absolute thickness will take a long time. Accordingly, for practical reasons, the detection of immunological reactions at a surface using an ellipsometer has not been adopted for diagnostic purposes.

The present invention is based on the discovery that any arbitrary immunologically reactive antigen will adsorb onto a substrate in a monomolecular layer only, and that a specific antibody for such arbitrary antigen will bond thereto to form a bimolecular layer on the substrate. In practicing this invention, such layers are easily and quickly detectable. This discovery then provides methods and apparatus of great utility in medical diagnostic and pharmacological applications.

Accordingly, it is a first principal object of this invention to provide method and apparatus for economically detecting immunological reactions occurring at a surface.

It is an object of this invention to provide such method and apparatus wherein such immunological reactions are detectable by electrical means.

It is another object of this invention to provide such method and apparatus for detecting such immunological reactions by direct visual observation.

A second principal object of this invention is to provide method and apparatus for detecting the presence or absence of antigens and antibodies by means of controlled immunological reactions occurring at a surface.

SUMMARY OF THE INVENTION

In accordance with this invention, a diagnostic method is provided for determining the presence or absence of a specific antibody in a biological sample comprising the steps of depositing a metal on a substrate material, contacting the substrte material with an aqueous medium containing a corresponding specifically reacting antigen to said specific antibody to coat all or part of the substrate material with a monomolecular layer of the specifically reacting antigen, immersing the coated substrate material in the biological sample, and then examining the coated substrate to determine whether the substrate has a bimolecular or monomolecular layer adhering thereto. If a bimolecular layer is detected, the diagnosis is that the biological sample does, in fact, contain the specific antibody of interest. Lack of a bimolecular layer is evidence that the simple does not contain the same.

The novel features of this invention sought to be patented are set forth with particularity in the appended claims. The invention, together with further objects and advantages thereof, may be understood from a reading of the following specification and appended claims in view of the accompanying drawings wherein like parts in each of the several figures are identified by the same reference character.

DETAILED DESCRIPTION OF THE INVENTION

Figure 1:
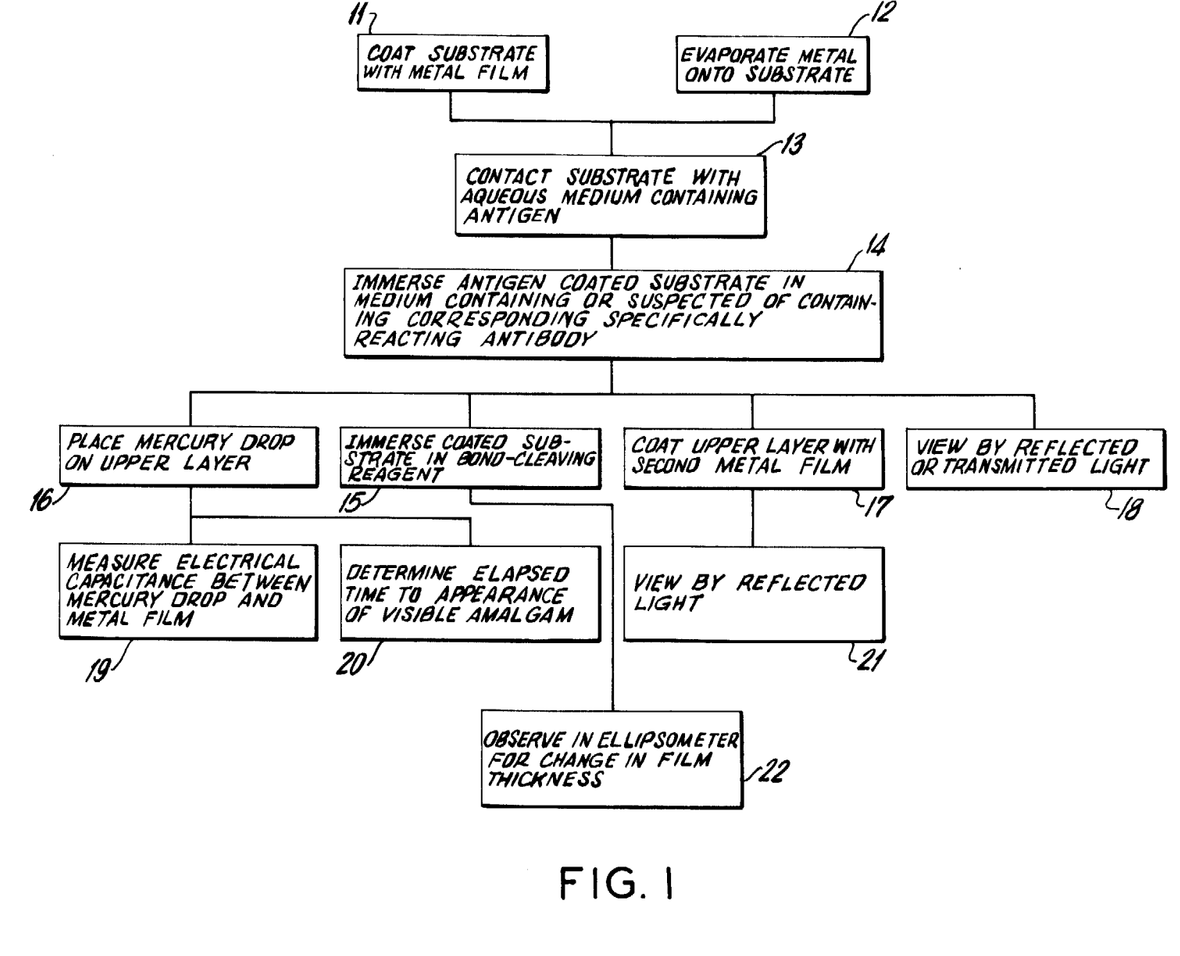
FIG. 1 is a flow chart illustrating the process steps of the various embodiments of this invention.

Referring now to FIG. 1, in reading the flow chart from top to bottom, each vertical level represents one time sequential step of the process. The appearance of several steps arrayed horizontally at a given vertical level in the flow chart indicates the alternative performance of one of the indicated steps at the indicated sequential position in accordance with the various embodiments of this invention.

In accordance with a first embodiment of this invention, the process begins at block 13 of FIG. 1 in which a wafer of substrate material which may be metal, glass, mica, plastic, fused silica, quartz, or similar material, with metal being preferred, as having the greatest difference in refractive index to the antigen or antibody, and preferably is in the form of a metallized glass slide, is contacted with a solution containing a first antigen of interest which is available in a relatively concentrated aqueous medium, e.g., a solution, and which is to be used to detect or purify its corresponding specifically reacting antibody. Contacting may be by any technique, such as applying one or more drops of medium or by partial or total immersion. Depending upon the technique and the concentration thereof, the first antigen adsorbs onto all or part of the surface of the substrate in a monomolecular layer. Any antigen will adsorb in such monomolecular layer but no further adsorption will take place. That is, the antigen will attach to the substrate, but will not attach to itself. The time required to adsorb the monomolecular layer on the substrate is a function of the concentration of the antigen in the solution and the degree of agitation of the solution. As an example, a 1 percent bovine serum albumin solution completely coats a slide in approximately 30 minutes with a monomolecular protein layer. The next step, illustrated in block 14 of FIG. 1 is to immerse the antigen coated substrate in a solution suspected of containing the specifically reacting antibody to the first antigen. This solution may, and typically does, contain many constituents in addition to the specifically reacting antibody whose presence it is desired to detect. However, no antibody other than a specifically reacting antibody will adhere to the first layer on the substrate. Of course, as is known, certain biological substances, may adhere by a phenomenon known as non-specific sticking. Such substances are found in sera, etc. There are a number of ways to minimize non-specific sticking, the most convenient of which appears to be in diluting the media carrying such substances. In any event, if the corresponding specifically reacting antibody is not present, the substrate following immersion in the suspected solution will still contain only a monomolecular antigen layer thereon. If, on the other hand, the corresponding specifically reacting antibody is present in the solution, immunological complexing between the first antigen and its corresponding specifically reacting antibody will take place and the substrate will, after a time, have a bimolecular layer thereon. It is to be noted that the steps illustrated in blocks 13 and 14 of FIG. 1 are common to all of the embodiments of this invention. The time requirement for the adhesion of a complete second molecular layer onto the coated substrate is again a function of the concentration of corresponding specifically reacting antibody in the solution. For antibodies in blood serum, this time may be as long as one day, or as short as minutes, depending on the concentration. In one embodiment of this invention, the next step is to immerse the coated substrate in a reagent capable of cleaving immunological bonds as illustrated in block 15 of FIG. 1 while simultaneously observing the coated substrate in an ellipsometer as illustrated in block 22 of FIG. 1. Such a reagent can be a weak acid solution, a base solution or a strong salt solution, and the like. While the formation of the specifically reacting antibody on the antigen coated substrate may take an extended period of time, the immunological bond between the two layers is severed very quickly by the immunological bond-cleaving solution. Accordingly, the observation made with the ellipsometer can be the relatively simple observation of change of film thickness rather than the more complicated measurement of absolute thickness. At the same time, observing the stripping away of the specifically reacting antigen/antibody layer by action of the immunological bond cleaving solution may be performed much more rapidly than the prior art method of observing the building of the specifically reacting antibody layer. Accordingly, a large plurality of test slides may be prepared in accordance with block 13 and each exposed to one of a large plurality of solution, e.g., serum samples as indicated in block 14, and then in a short time each test slide may be examined serially in accordance with blocks 15 and 22 to determine which of the serum samples contained the specifically reacting antibody to the first antigen. Since the immunological bond cleaving reagent will not strip the first antigen or antibody from the substrate, those coated substrates which were immersed in media which did not contain the specifically reacting antibody will exhibit no change of film thickness when immersed in the cleavage reagent and observed in an ellipsometer. On the other hand, those which were immersed in a solution which did contain the specifically reacting antibody will exhibit approximately a factor of 2-5 change in thickness when immersed in the cleavage reagent and observed in an ellipsometer. Each observation can be made in a few minutes thereby providing an efficient, and therefore diagnostically significant, test procedure.

While the first described embodiment improves the efficiency of ellipsometer immunological detection to the point of practical feasibility, it is nevertheless economically desirable to eliminate the need for the ellipsometer entirely. Accordingly, another embodiment of this invention provides for determination of relative film thickness by electrical means. In this embodiment, either a metallic substrate is chosen, or a substrate of another material is first coated with a metal film as indicated in block 11 of FIG. 1. The metal substrate or metal-coated substrate is then coated with media containing antigens in accordance with the steps of blocks 13 and 14 as discussed above. The layers adhering to the substrate are electrically insulating. The next step is to place a mercury drop or other electrode upon the upper antigen layer adhering to the substrate as shown in block 16 of FIG. 1. The upper layer is either the first antigen, if the suspected solution contained no corresponding specifically reacting antibody, or the specifically reacting antibody if the solution did contain it. Accordingly, the metal film or metal substrate and the mercury drop comprise the two conducting plates of an electric capacitor separated by an insulating layer comprising either a monomolecular layer or a bimolecular layer of the antigen or antibodies. The electric capacitance of this capacitor is then measured as indicated at block 19 of FIG. 1 by means of any suitable instrument for measuring capacitance as is known in the art, for example, Heathkit Impedance Bridge Model IB-28. The electrical capacitance of such capacitors having a bimolecular layer dielectric is, as expected, found to vary by approximately a factor of 2-5 from that of such capacitors having a monomolecular layer.

Another, closely related, embodiment of this invention further simplifies the detection of the specifically reacting antibody by enabling its presence to be ascertained by unaided visual observation. This embodiment employs a substrate of a metal which forms an amalgam with mercury or another substrate material such as glass which is coated in the block 11 step with a thin film of metal which forms an amalgam with mercury, preferably gold. The substrate is then subjected to the block 13 and block 14 steps as before and a mercury drop is again placed on the upper layer as indicated in block 16. In this embodiment, however, no electrical measurement is made. In this embodiment, the next step is to visually observe the coated substrate and determine the length of time which elapses before a visible amalgam is formed between the mercury and the metal film coated on the substrate. This embodiment of the invention depends upon the inventive discovery that mercury diffuses through a monomolecular layer in approximately 1 minute, but requires 10 minutes or longer to diffuse through a bimolcular layer. Since the mercury must diffuse through the layer or layers to form a visible amalgam with the metal film coating on the substrate, the time between the placing of the mercury drop upon the upper layer and the appearance of the visible amalgam indicates whether a monomolecular or bimolecular layer is present on the substrate and consequently whether or not the suspected solution actually contained corresponding specifically reacting antibody to the first antigen. At this point, those skilled in the art will realize that the capacitance measurement of the last previously discussed embodiment must be made within 1 minute of the placing of the mercury drop upon the upper layer lest the mercury electrode diffuse through the insulating layer and short out the capacitor. Alternatively, shorting may be prevented by coating the metal with a metal oxide insulating layer and adhering the antibody or antigen onto the metal oxide. It will also be recognized that a rough quantitative measure of the concentration of specifically reacting antibody in the suspected solution may be made in accordance with this embodiment by preparing a plurality of substrates in the block 13 step and immersing them simultaneously in the suspected solution as indicated in block 14, but removing them sequentially from the solution over an extended period of time. Since the rate at which the corresponding specifically reacting antibody layer forms is a function of the concentration of specifically reacting antibody in the solution, a comparison of diffusion times for the mercury drop through the layers on a series of substrates having been exposed to the suspected solution for varying periods of time will provide a rough quantitative indication of the concentration of specifically reacting antibody in the suspected solution.

In another related embodiment, a substrate is coated with a metal film as depicted in block 11 of FIG. 1. As discussed in the last embodiment, the substrate is then contacted with the media as shown in blocks 13 and 14. The next step in accordance with this embodiment is to coat the upper antigen or antibody layer with a second metal layer as illustrated in block 17 of FIG. 1 and to view the structure thus produced by reflected light as illustrated in block 21 of FIG. 1. The second metal is preferably applied by electroplating. Essentially, this embodiment produces a structure which functions as a diffraction grating and the difference between a monomolecular and bimolecular antigen or antibody insulator layer is determinable from the spectral components observable in the reflected light.

Figure 5A:
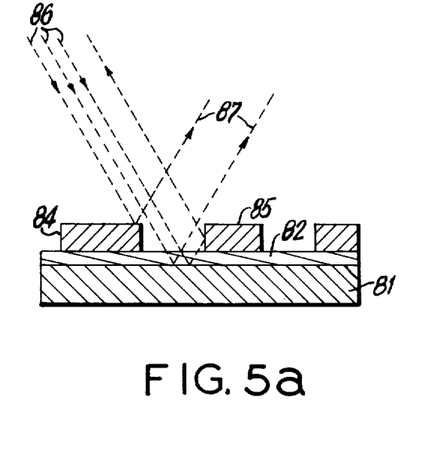
FIGS. 5a and 5b are elevation views of diagnostic apparatus.
Figure 5B:
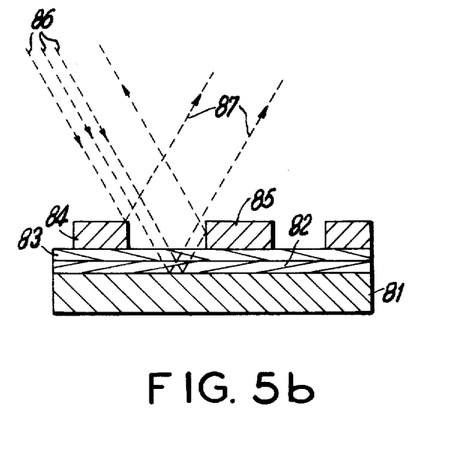

FIGS. 5a and 5b illustrate apparatus in accordance with this embodiment. A metallic surface 81 of a substrate which may be either a metallic substrate or a non-metallic substrate coated with a metal film, has a first antigen layer 82 applied thereto as indicated in block 13 of FIG. 1. The substrate having layer 82 is then immrsed in the solution to be tested and a second layer 83 of corresponding specifically reacting antibody to the antigen of layer 82 forms thereon if it is present in the solution. A second layer of mtallization is then applied to the exposed surface of the film. A very small quantity of metal is applied so that the second metallization tends to be in the form of a plurality of discontinuous metallized areas, as, for example, 84 and 85. A beam of light represented by rays 86 is then directed onto the slide thus prepared. The light is reflected at metal boundaries. The distance between the reflecting surfaces of metal substrate surface 81 and metallization particles, 84, for example, is a function of the thickness of the film between members 81 and 84. Accordingly, the observed reflected light, illustrated by rays 87, varies in spectral composition as the antigen or antibody layer varies between a monomolecular layer and a bimolecular layer.

Another embodiment of this invention illustrated in FIG. 1 comprises the steps illustrated at blocks 12, 13, 14 and 18 of FIG. 1. In this embodiment, the substrate which must be a light transmissive substrate such as glass, plastic, fused silica, mica, quartz, or the like, and is preferably glass, with microscope slides being a conveniently available source, is first coated with a plurality of metal globules by evaporating a metal, for example, indium, onto the substrate as indicated in block 12 of FIG. 1. For example, the indium is evaporated slowly from a tantalum boat onto the glass substrate in an ordinary vacuum of about $5 \times 10^{-5}$ mm of mercury. Because the indium atoms have high mobility on the surface of the substrate and do not wet the glass substrate significantly, the indium evaporated onto the substrate agglomerates into small particles. Any metal having similar characteristics so that it will form globules on the substrate when evaporated thereon may be used. In addition to indium, gold, silver, tin, lead, and bismuth may be used. The evaporation of metal is continued until the substrate appears light brown in color. At this point, the metal globules have diameters on the order of 1000 A. The precise size of the globules is not critical but they must have diameters equal to a large fraction of the wavelengths of visible light. The next step is to contact the globule-covered substrate with a medium containing an antigen as illustrated in block 13 of FIG. 1. The antigen again adheres in a monomolecular layer over the substrate and the metal globules thereon. When a monomolecular layer has formed, the coated substrate may then be used to test suspected solutions for the presence of a corresponding specifically reacting antibody to the antigen by immersing the coated substrate in the suspected solution as indicated in block 14 of FIG. 1. If the suspected specifically reacting antibody is present, the substrate and metal globules have a bimolecular layer adhering threto; if the specifically reacting antibody is not present, only a monomolecular layer overlies the substrate and metal globules. The coated substrate is then viewed by either reflected or transmitted light as indicated in block 18 of FIG. 1 and a determination is made from the appearance of the coated substrate as to thickness of the layer adhering thereto and accordingly as to the presence or absence of the suspected specifically reacting antibody. The detection of layers corresponds to variations in the shade of brown which is observed in the coated substrate. These variations are quite pronounced and the detection of layers is therefore a simple straightforward procedure. The particles alone on the substrate appear as a first shade of brown, the particles coated with a monomolecular antigen layer appear as a darker shade of brown, and the particles covered with a bimolecular layer appear as a still darker shade of brown. This detection method is based on the fact that electromagnetic radiation is scattered to a large degree by conducting spheres having diameters equal to a large fraction of a wavelength of the incident light and that in the case of scattering from such spheres, the scattering is strongly influenced by a thin dielectric coating applied to the spheres.

Figure 4:
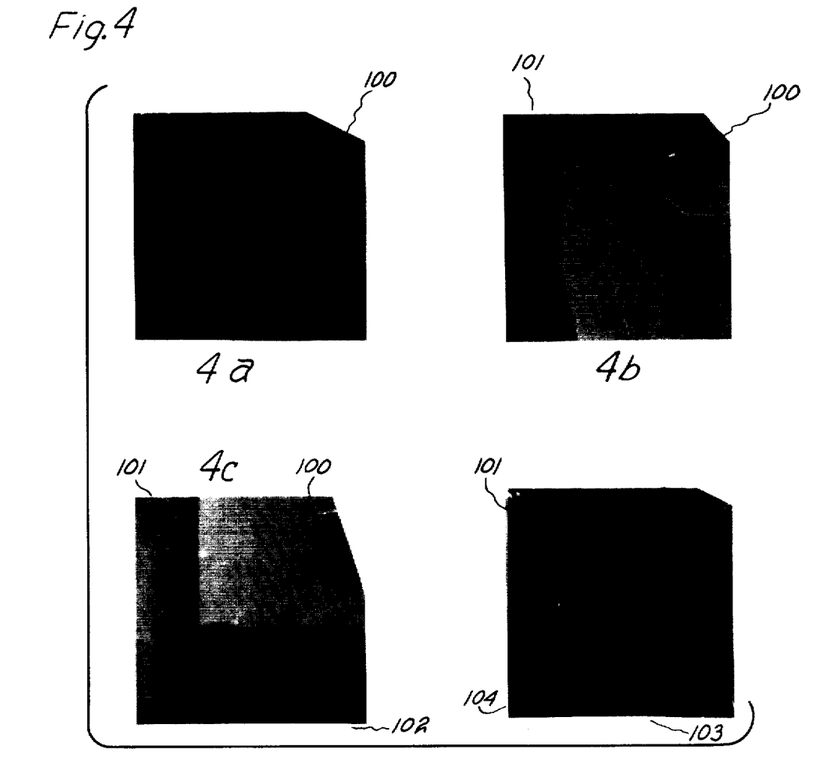
FIG. 4 is a photograph illustrating the operation of diagnostic apparatus in accordance with this invention.

FIG. 4 is a reproduction of an actual photograph of diagnostic apparatus in accordance with this embodiment. In each view of FIG. 4 the test slide is viewed by transmitted light. View 4a is a glass slide having indium globules over one surface 100 thereof. View 4b shows a slide prepared as the slide of view 4a whose left edge has been immersed in a solution of bovine serum albumin, thereby adsorbing a monomolecular layer 101 of bovine serum albumin thereon. View 4c shows a similar slide in which the left edge has been immersed in bovine serum albumin thereby adhering a monomolecular layer 101 of bovine serum albumin thereon, and whose lower edge has been immersed in a solution of ovalbumin thereby adsorbing a monomolecular layer 102 of ovalbumin thereon. It is important to note that the appearance of the coated portions of the slide of view 4b are similar, indicating that only a monomolecular protein layer is present on the slide. This demonstrates that bovine serum albumin and ovalbumin absorb onto the slide and that the ovalbumin does not adhere to the portion of the slide previously coated with bovine serum albumin. In other words, view 4c illustrates the discovery discussed above that any arbitrary antigen or antibody will adhere to the substrate but another antigen or antibody will not adhere to an arbitrary antigen or antibody film, except for immunological complex formation and the possibility, as noted above, for some non-specific sticking to occur. The slide of view 4d was prepared by immersing fthe left edge thereof in bovine serum albumin in solution to adhere monomolecular layer 101 thereon; the right edge was then immersed in an ovalbumin solution to adhere monomolecular layer 102 thereon; and finally the lower edge was immersed in a solution of rabbit anti-serum to bovine serum albumin. Accordingly, 103 is a monomolecular layer of rabbit anti-serum to bovine serum albumin. The appearance of the lower right-hand corner indicates that the rabbit anti-serum to bovine serum albumin did not adhere to ovalbumin layer 102 and accordingly the lower right-hand corner of the slide of view 4d is coated with only a monomolecular layer of ovalbumin. The lower left-hand corner of view 4d is pronouncedly darkened indicating the presence thereon of a bimolecular protein layer comprising a first monomolecular layer of bovine serum albumin, previously adsorbed thereon, having a second monomolecular layer of rabbit anti-bodies to bovine serum albumin immunologically complexed with the underlying bovine serum albumin. It will accordingly be seen that only the specifically reacting protein pair formed a bimolecular layer on the slide, all other coatings thereon being monomolecular.

In a modification of this embodiment which provides for a medical diagnostic system, the substrate having metal spheres thereon is partially immersed, to a first depth, in a solution of a first antigen. The substrate is coated in a monomolecular layer by the first antigen over the area which is immersed in the solution. The substrate is then dried and is more deeply immersed, to a second depth, in a solution of a second antigen. The second antigen does not adhere to the first antigen but does adhere to the uncoated portion of the substrate which is immersed in the solution. The substrate is then again dried and immersed in a solution of a third antigen to a third and greater depth. The third antigen adheres to that portion and only the portion of the substrate which is not coated with the first or second antigen. The process is repeated for any number of antigens of interest. The resulting product is a substrate coated with a plurality of bands of monomecular layers of different antigens. This coated slide is the diagnostic tool. The medical diagnostic procedure is then to immerse the slide in a specimen of, for example, blood for a period of typically several hours in duration. The slide is then removed from the specimen and after washing in water is viewed by reflected or transmitted light. The slide then exhibits a pattern of lighter and darker bands which are indicative of the antibodies present in the specimen from which information a medical diagnosis is made.

Figure 2A:
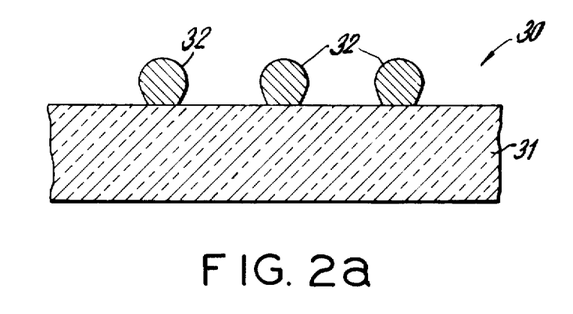
FIGS. 2a, 2b and 2c are elevation views of diagnostic apparatus in accordance with this invention illustrating the method of making and using same.
Figure 2B:
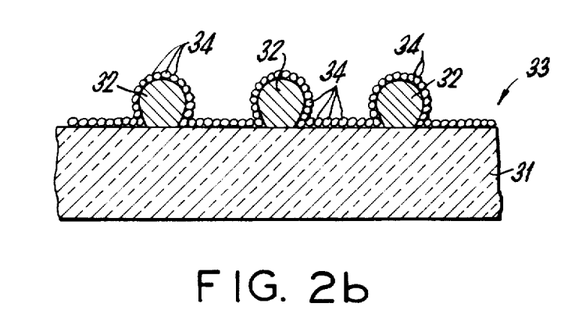
Figure 2C:
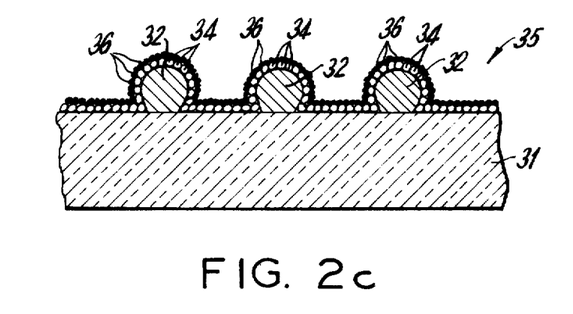

FIGS. 2a, 2b and 2c are highly magnified elevation views of a portion of diagnostic apparatus in accordance with the last discussed embodiment of this invention. FIG. 2a shows a portion of substrate material 31 having a plurality of globules of evaporated metal 32 attached thereto. Particles 32 are preferably formed by the evaporation of indium onto substrate 31 as discussed above but may also be formed by evaporation of gold, silver, tin, lead, or other metal having similar nonwetting and atomic mobility characteristics. Any of a large number of metals will exhibit such characteristics as the temperature of the substrate is varied. After contact with a medium containing an antigen, the slide segment comprising substrate 31 and metal globules 32 is partially or completely coated with a monomolecular layer of molecules 34 of the antigen as indicated in FIG. 2b generally at 33. The apparatus indicated at 33 is the diagnostic instrument which is used to test suspected solutions for the presence of corresponding specifically reacting antibodies to antigen layer 34. If the apparatus indicated generally at 33 is exposed to specifically reacting antibody to the antigen layer 34, the apparatus will acquire the appearance indicated generally in FIG. 2c at 35 in which substrate 31 and metal globules 32 are coated with a bimolecular layer comprising the layer 34 of the antigen forming a first monomolecular layer overlying substrate 31 and globules 32 and a second monomolecular layer consisting of the layer 36 of the specifically reacting antibody to the first immunologically bonded to the molecules of the first and overlying the first layer, the metal globules, and the substrate.

Figure 6:
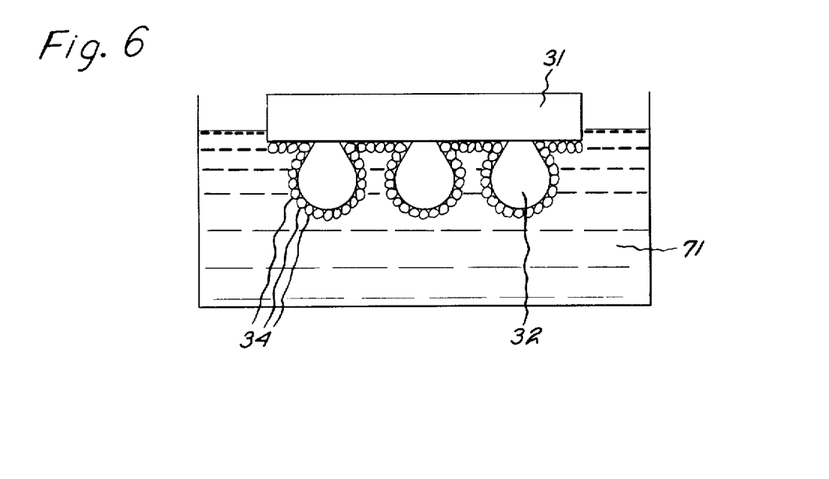
FIG. 6 is an elevation view of diagnostic apparatus in accordance with this invention illustrating a modification in the method of using the apparatus of FIG. 2.

FIG. 6 illustrates a modification of this embodiment of the invention which provides for increased contrast in the coated diagnostic slide. In FIG. 6, slide 31 having metal globules 32 applied thereto and coated with antigen monomolecular layer 34, as in FIG. 2b, is immersed, the coated side downwardly, in a quantity 71 of light reflecting liquid. Slide 31 is then viewed from its upper surface by reflected light. In order to provide for total reflection of light incident on the diagnostic apparatus of FIG. 6, reflecting liquid 71 is preferably a metallic liquid, and is more particularly, preferably mercury. If a non-metallic liquid is employed, the optical incidence and viewing angles employed in using the FIG. 6 embodiment become critical if total reflection is to be observed. The appearance of a test slide viewed in accordance with these teachings is similar to that shown in FIG. 4, but with enhanced contrast.

Figure 3A:
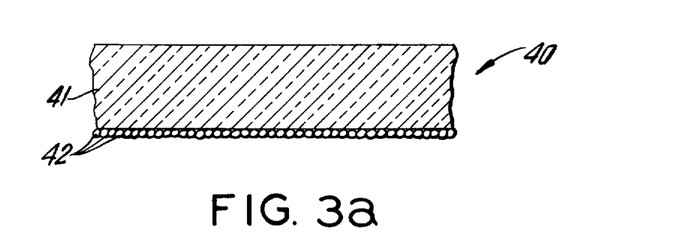
FIGS. 3a, 3b and 3c are elevation views of apparatus useful for diagnostic purposes in accordance with another embodiment of this invention.
Figure 3B:
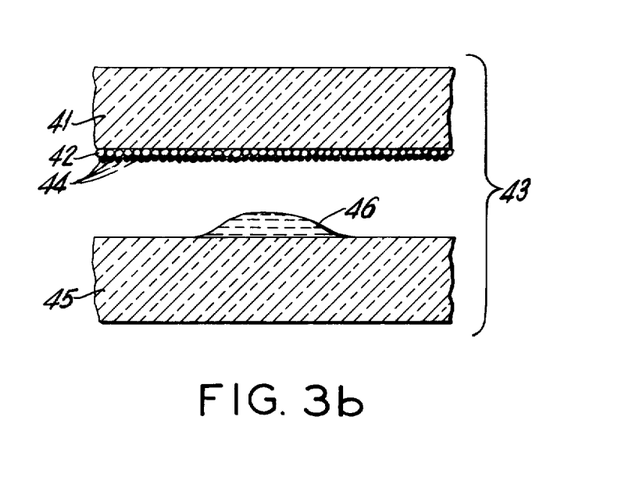
Figure 3C:
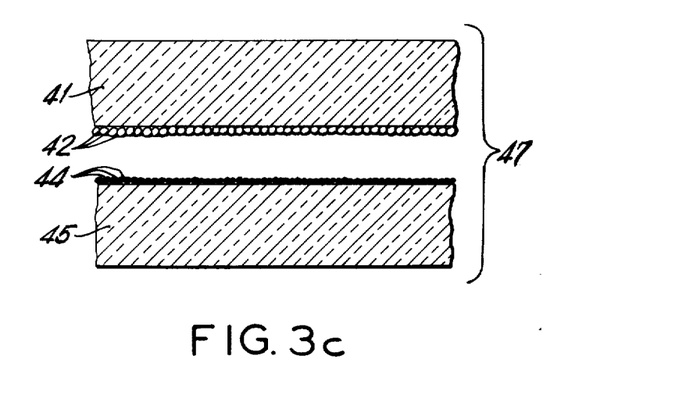

FIGS. 3a, 3b and 3c are highly magnified sectional elevational views of apparatus useful for diagnositc purposes in accordance with another embodiment of this invention. Indicated generally in FIG. 3a at 40 is a substrate 41 coated with a monomolecular layer of antibody molecules 42 which has been prepared as discussed above. Indicated generally in FIG. 3b at 43 is substrate 41 and antigen layer 42 to which has been immunologically bonded a second monomolecular layer of molecules 44 in accordance with the procedures discussed above. A second substrate 45 has thereon a drop 46 of a reagent capable of cleaving immunological bonds, e.g., a weak acid solution. The mutually facing surfaces of substrates 41 and 45 having thereon respectively a bimolecular layer and a reagent drop of, for example, citric acid in a 0.1 normal solution, are then physically brought into contact with each other. In accordance with an inventive discovery of this invention, the reagent drop 46 severs the immunological bonds between molecules 42 and molecules 44 without affecting the bimolecular characteristics of either antigen or antibody and without severing the adhesion bond between the first molecules 42 and substrate 41. When substrates 41 and 45 are again separated as indicated in FIG. 3c generally at 47, substrate 41 has adhering thereon a monomolecular layer of antigen molecules 42 and substrate 45 has adhering thereon a monomolecular layer of corresponding specifically reacting antibody molecules 44. Substrate 41 with molecules 42 thereon may then be used again as a test slide in accordance with the other previously discussed embodiment of this invention. Substrate 45 with specifically reacting antibody 44 ahdering thereto may also be used as a test slide to test suspected solutions for the presence of molecules of its corresponding antigen in accordance with the other previously discussed embodiments of this invention. This embodiment of this invention is considered to be particularly significant because, as has already been noted, in the case of the usual immunogens of biological interest, antigens are fairly readily available in purified form and so may be absorbed onto a substrate to form a test slide for the detection of the presence of antibodies in suspected solutions but antibodies are not so available. Therefore, previously to this invention it has generally not been possible to produce test slides for testing suspected solutions for the presence of antigens. The method and apparatus illustrated in FIG. 3, however, provides for the production of test slides comprising substrate 45 coated with a monomolecular layer of, for example, antibody molecules 44 which may be used to test suspected solutions for the presence of antigen.

Figure 7:
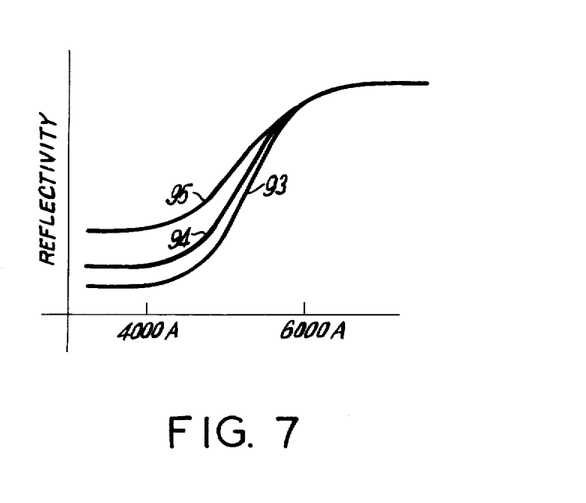
FIG. 7 is a graphical representation illustrating the principle of operation of diagnostic apparatus in accordance with the embodiment of this invention illustrated in FIG. 8.
Figure 8:
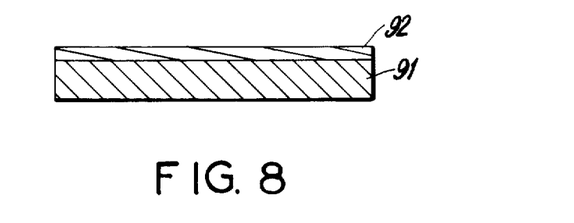
FIG. 8 is an elevation view of another embodiment of diagnostic apparatus in accordance with this invention.

Another embodiment of diagnostic apparatus in accordance with this invention is illustrated structurally in FIG. 8, and its principle of operation is illustrated graphically in FIG. 7. As illustrated in FIG. 8, diagnostic apparatus in accordance with this invention comprises a gold substrate 91, which, for reasons of economy, is preferably a thin gold layer plated onto another metal, and which has adsorbed thereon a monomolecular layer 92 of first antigen or antibody. Gold has an absorption band within the visible spectrum. This fact accounts for the characteristic color of gold and provides for the operation of this embodiment of this invention.

FIG. 7 illustrates the operation of this embodiment and constitutes a set of reflectivity curves in which relative reflectivity is plotted as a function of wavelength. Curve 93 represents the reflectivity of gold metal. Curve 94 represents the reflectivity of gold metal having a monomolecular antigen layer thereon. Curve 95 represents the reflectivity of gold metal having a bimolecular layer thereon. Accordingly, a gold substrate such as 91 has, in accordance with curve 93, the characteristic bright yellow color of gold metal. When the first antigen layer 92 is applied to substrate 91, the appearance of the test slide, in accordance with curve 94, has a dull yellow appearance. After the test slide has been exposed to a solution suspected of containing corresponding immunologically reacting antibody to the antigen comprising layer 92, the test slide, if such specifically reacting antibody was present in the solution, has a bimolecular layer thereon and a reflectivity characteristic indicated by curve 95 which provides a distinctly green appearance.

In tests which have been performed to date, it appears that the embodiments of this invention which employ a substrate including metal globules, that employing a gold substrate, and that employing a metal, e.g., titanium, overlaid with an oxide coating, e.g., an oxide of titanium, are the most generally useful. Furthermore, it has been determined that these embodiments have differing sensitivities as functions of the thicknesses of films of interest. Specifically, the greatest sensitivity of the embodiment having a substrate including metal globules occurs with films having thicknesses below approximately 200 A. The gold and other substrate embodiments have the greatest sensitivity for films exceeding 30 A in thickness.

DESCRIPTION OF THE PREFERRED EMBODIMENTS

The following examples, which are to be regarded as illustrative and not limiting, show how surface immunological tests are carried out according to this invention.

EXAMPLE 1

An inhibition test for hepatitis is carried out as follows: Glass slides are coated with a thin indium layer and overcoated with a gold layer. The use of indium undercoating is required to improve the adhesion between the glass and the gold. It is found further that the diffusion of the indium into the overlying gold improves the optical characteristics of the test slides. The slides thus prepared are coated with a monomolecular layer of hepatitis-associated antigend. Samples of human blood to be tested for the presence of hepatitis are prepared by mixing therein a quantity of antibodies to hepatitis-associated antigen sufficient to be immunologically removed from the mixture if hepatitis-associated antigen be present in the sample. The test slides are then immersed in the previously prepared blood samples. When removed, the slides which have been immersed in hepatitis negative samples have a bimolecular protein layer thereon comprising the hepatitis-associated antigen previously applied thereto and a second layer of antibodies to hepatitis-associated antigen immunologically bonded thereto evidenced by a greenish band on the slide. Slides having been immersed in hepatitis positive samples, on the other hand, retain their original dull yellow appearance indicating that only the monomolecular hepatitis-associated antigen layer is present thereon, the antibodies which have been introduced into the sample having complexed with the antigen therein and precipitated out of the sample to be unavailable to react with the antigen on the test slide.

EXAMPLE 2

In a direct test for hepatitis, glass-indium-gold slides are prepared as described in Example 1 and then coated with a monomolecular layer of antibodies to hepatitis-associated antigen. Some of the slides are then immersed into pooled serum taken from hepatitis patients and therefore known to contain hepatitis-associated antigen. Others of the slides are immersed in serum samples known to be free of hepatitis-associated antigen. Those slides which have been immersed in the pooled serum have bimolecular protein layers thereon, detectable visually as darker zones as described above, while those immersed in the other blood had only monomolecular layers thereon.

Theoretically, the direct test described in Example 2 is the preferred diagnostic procedure both because of the relative simplicity thereof and also because, in this case, the direct test has a higher sensitivity than the inhibition test of Example 1. The higher sensitivity of the direct test results from the fact that hepatitis antigen molecules are very much larger than molecules of antibody to hepatitis-associated antigen. Therefore, the direct test involves a much larger percentage change in film thickness, and accordingly greater contrast is observable.

The concentration of hepatitis-associated antigen in the blood of a person having been exposed to the disease is a function of time. The concentration of hepatitis-associated antigen is quite high during the clinical and immediately preclinical phases of hepatitis. In the far post-clinical phases, however, the concentration of hepatitis-associated antigen in the person's blood is very low. Both conditions are medically of interest. Detection of the antigen during the clinical and immediately preclinical phases is of value for the purposes of diagnosis. Detection of the antigen in the far post-clinical phase is of value for screening the blood of prospective blood donors. As a practical matter the simpler, more sensitive direct test is preferable for diagnostic purposes since it may be readily performed because of the relatively high concentration of hepatitis-associated antigen in the blood sample.

EXAMPLE 3

The inhibition test of Example 1 described for screening purposes is evaluated experimentally to determine its value relative to other known screening tests for hepatitis. In these tests, hepatitis positive pooled serum is diluted with known hepatitis negative serum. Using the inhibition procedure of Example 1, a dilution of one part hepatitis positive pooled serum to 32 parts known hepatitis negative serum results in reliable detection over a one-hour period. Using a dilution of one part hepatitis positive pooled serum to 3000 parts known negative serum, reliable detection is obtained over a twenty-hour period. These results will be seen to be very similar in sensitivity and time consumed, respectively, to the presently known counterelectrophoresis procedure and radioimmunoassay procedure. Therefore, a screening procedure in accordance with this invention is seen to provide results comparable to the best obtainable with prior art procedures, with the additional advantage of obtaining the results through a significantly less expensive procedure.

The use of a gold coated substrate in preference to a metal globule coated substrate in the aforedescribed hepatitis diagnostic procedure is preferred because hepatitis-associated antigen molecule are approximately 210 A in diameter. Such film thicknesses are well within the capability of gold coated substrates to provide sensitive indication, but are too thick for high sensitivity of indication using the metal globule coated substrate.

EXAMPLE 4

A diagnostic test for gonorrhea is carried out as follows: A glass slide is metallized with a layer of titanium and the surface layer is then oxidized to produce a cover layer of an oxide of titanium. Neisseria gonorrhoeae extract is dissolved in salt water to produce a concentration of 1 mg./ml. A drop of the solution of antigen is placed in the center of the slide. The slide is incubated in a moist chamber (plastic box filled with wet sponges) at room temperature (23° C.) until the antigen adheres to the oxide surface (10–30 minutes). The slide is washed with distilled water and blown dry with a jet of air. The slide can be stored at this point for later use. To use, the test slide is immersed in blood serum which contain antibody to the Neisseri antigen; the total volume is 2 ml. The slide and antibody solution are incubated at 23° C. in a plastic box attached to a shaker, for 12 hours. After incubation, the slide is again washed with distilled water. If, after drying, a sharply contrasting visible spot is observed in the center of the slide, this indicates a positive reaction. In cases where the blood serum does not contain gonorrhea antibodies, no bimolecular layer will form, and no spot will be seen.

EXAMPLE 5

A diagnostic test for rubella is carried out by the general procedure of Example 4. A gold metallized glass slide is used and the antigen is an extract of a rubella viral culture. After treatment of the slide with a human serum preparation containing rubella antibody, a sharply contrasting visible spot is observed. The procedure is repeated substituting a tantalum metallized glass slide. Substantially the same results are obtained.

At present, rubella antibodies are detected using a hemagglutination-inhibition (HAI) test. It is performed on patients in obstetrics clinics as well as females of child-bearing age who pass through health clinics. Such tests require two days; the test of this invention requires two hours. Moreover, there is a high correlation with HAI results.

EXAMPLE 6

A diagnostic test for poliomyelitis is carried out by the general procedure of Example 4. A gold metallized glass slide is used and the antigen is an extract of a polio viral culture. After treatment of the slide with a human serum preparation containing polio antibodies, a sharply contrasting visible spot is observed. The procedure is repeated substituting a tantalum metallized glass slide, with substantially the same results.

This test procedure is much simpler than the usual method in which polio antibody level is determined by a complement-fixation test.

EXAMPLE 7

A test is made for vesicular stomatitis proteins by the general procedure of Example 4. A gold metallized glas slide is used and the antigen is an extract of vesicular stomatitis virus. After treatment of the slide with proteins specific to the antigen, a sharply contrasting visible spot is observed. Tantalum metallized glass slides can be substituted, and substantially the same results are obtained.

EXAMPLE 8

A diagnostic test for tetanus is carried out by the general procedure of Example 4. A gold metallized glass slide is used and the antigen is applied as an aqueous extract of tetanus toxoid. After treatment with a human serum preparation containing tetanus toxoid antibodies, a sharply contrasting visible spot is observed. The procedure is repeated substituting a tantalum metallized glass slide, with substantially the same results.

EXAMPLE 9

A diagnostic test for diphtheria is carried out by the general procedure of Example 4. A tantalum metallized glass slide is used and the antigen is an aqueous extract of the diphtheria bacterial toxin. After treatment with a human serum preparation containing antibodies to diphtheria toxins, a sharply contrasting visible spot is observed.

EXAMPLE 10

A diagnostic test for syphilis is carried out by the general procedure of Example 4. A gold metallized glass slide is used and the antigen is an aqueous suspension of Treponema pallidum. After treatment with a human serum preparation containing antibodies to syphilis, a sharply contrasting visible spot is observed. Tantalum metallized glass slides can be substituted, and substantially the same results are obtained.

EXAMPLES 11 AND 12

Diagnostic tests for fungal antibodies are carried out by the general procedure of Example 4. A tantalum metallized glass slide is used and the antigens, respectively, are aqueous suspensions of the family Aspergillus and Candida. After treatment with a preparation of human blood sera containing the corresponding fungal antibodies, sharply contrasting visible spots are observed.

EXAMPLE 13

A diagnostic test for a parasite is carried out by the general procedure of Example 4. A gold metallized glass slide is used and the antigen is an aqueous extract of *Toxoplasma gondii*. After treatment with a human serum preparation containing antibodies to this parasite, a sharply contrasting visible spot is observed. The procedure is repeated substituting tantalum and indium metallized glass slides with substantially the same results.

Quantitative tests are also carried out on gold and tantalum metallized glass slides, by making two-fold dilutions of the patient's serum (antibody) and using as the endpoint of the titration that concentration corresponding to that providing the last visible spot.

The parasite has an unknown etiology but it has been determined that latent and/or unsymptomatic infections in pregnant women cause many birth defects. No other serological method has been developed to test for antibodies to this organism.

EXAMPLE 14

A diagnostic test for antiobodies to human nucleoprotein-DNA is carried out by the general procedure of Example 4. A gold metallized glass slide is used and the antigen is an aqueous suspension of the DNA-histone complex found in the nuclei of human cells. After treatment with preparations of human blood sera containing antibodies to the DNA-histone complex (nucleoprotein) and/or antibodies to DNA (uncomplexed with histone), sharply contrasting visible spots are observed. The advantage in this technique is that both nucleoprotein and DNA antibodies can be determined on a single slide. The procedure is repeated substituting tantalum metallized glass slides with substantially the same results.

In certain disease conditions, autoantibodies to these human molecules can be directed to the DNA portion of the molecule to the histone, or to the bond between the two. In 30% of the cases of Lupus erythematosus, an antibody is produced which is specific to DNA and as such its detection is diagnostically useful. Current methods for testing for such antibodies involve a slide technique using mouse liver tissue and a special peroxidase stain, or a fluorescent antibody technique. Both procedures are long and the slides are difficult to read. In contrast, the method of this example is much shorter, the slides are easier to read, and they show high correlations with the present methods of analysis.

EXAMPLE 15

A diagnostic test for antibodies to human protein thyroglobulin is carried out by the general procedure of Example 4. Such antibodies are formed in certain disease states, e.g., Hashimoto's disease. A gold metallized glass slide s is used and the antigen is an aqueous suspension of thyroglobulin. After treatment with a preparation of human blood serum containing antibodies to thyroglobulin, a sharly contrasting visible spot is observed. The procedure is repeated substituting tantalum metallized glass slides with substantially the same results.

EXAMPLE 16

A diagnostic test for antibodies to collagen is carried out by the general procedure of Example 4. A tantalum metalized glass slide is used and the antigen preparation is an aqueous medium containing collagen. After treatment with rabbit blood sera containing antibodies induced by administration of collagen fractions, a sharply contrasting visible spot is observed. Rabbits fed high cholesterol diets produce antibodies to collagen.

EXAMPLES 17 AND 18

An inhibition test is run to diagnose for pregnancy. A gold metallized glass slide is used and the antigen is an aqueous preparation of human chorionic gonadotrophin (HCG). Blood serum containing HCG is serially diluted and a known concentration of HCG antibody is added. The slide is immersed in the preparation. No visible spot is detected if the test is positive. A visible spot corresponds to a negative test. Levels of above 2000 International Units of HCG/100 ml. of serum indicate pregnancy. The method can also be adapted to test for tumors in prostate glands in males.

The procedure is repeated, substituting insulin for HCG. A blank slide corresponds to a positive test. Antibody titrations are successfully carried out on gold and tantalum-metallized glass slides, with a sensitivity of 100 nanogram, which can be readily increased.

EXAMPLE 19

A diagnostic test for antibodies to keyhole lymphet hemocyanin (KLH) protein is carried out by the general procedure of Example 4. A gold metallized glass slide is used and the antigen preparation is an aqueous medium of KLH protein. After treatment with a preparation of human blood serum containing antibodies to KLH protein, a sharply contrasting visible spot is observed. The procedure is repeated substituting tantalum metallized glass slides with substantially the same results.

At presnt, research is being conducted to find an antigen that can be used in humans to test the efficiency of their antibody response systems. Necessary to this end is an antigen which has not previously been encountered by the host, and KLH is a likely candidate. The present method is useful in this work because it is capable of detecting low levels of antibodies to KLH end is not cumbersome, time-consuming and insensitive.

While this invention has been described with reference to particular embodiments and examples, other modifications and variations will occur to those skilled in the art, in view of the above teachings.

Finally, although the reactive protein adsorbed on the substrate surface has been described hereinabove as being an antigen, it should be evident that such first layer reactive protein could be an antibody, and the second layer protein would then be the antigen specific to such antibody, and the third layer would again be the antibody. Accordingly, it should be understood that within the scope of the appended claims, the invention may be practiced otherwise than is specifically described.

I claim:

1. A diagnostic method for determining the presence or absence of a specific antibody or antigen in a biological sample comprising the steps of:
   depositing a metal onto a substrate material;
   contacting said substrate material with an aqueous medium containing either a corresponding specifically reacting antigen to said specific antibody or a corresponding specifically reacting antibody to said specific antigen, to coat all or part of said substrate material with a monomolecular layer of said specifically reacting antigen or antibody;
   immersing said coated substrate material in said sample; and
   examining said coated substrate material to determine whether said substrate has a bimolecular or monomolecular layer adhering thereto.

2. The method of claim 1 wherein said step of depositing a metal comprises evaporating a metal having high atomic mobility and poor surface wetting characteristics as metal globules onto a light transmissive substrate material.

3. The method of claim 1 to determine the absence or prsence of a specific antigen wherein the aqueous medium contains a corresponding specifically reacting antibody to said specific antigen.

4. The method of claim 1 wherein said step of depositing a metal comprises coating said substrate material with a metal film.

5. The method of claim 4 wherein the substrate material is slide like and also includes a metal oxide layer intermediate the metal of the slide and said monomolecular layer.

6. The method of claim 5 wherein said metal is titanium and said metal oxide is an oxide of titanium.

7. The method of claim 1 wherein said step of depositing a metal comprises evaporating a metal selected from the group consisting of indium, gold, silver, tin and lead, as metal globules onto a light transmissive substrate.

8. The method of claim 7 wherein said light transmissive substrate is selected from the group consisting of glass, plastic, fused silica, mica and quartz.

9. The method of claim 7 wherein said metal is indium and said examining step comprises visually examining said substrate and said determination is made by distinguishing between different shades of brown.

10. The method of claim 1 wherein said step of depositing a metal comprises coating said substrate with a thin layer of gold.

11. The method of claim 10 wherein said examining step comprises visually examining said substrate and said determination is made by reflectivity measurement.

12. The method of claim 10 wherein another metal is placed between said gold layer and said substrate.

13. The method of claim 12 wherein said another metal is indium.

14. The method of claim 1 to determine the absence or presence of a specific antibody wherein the aqueous medium contains a corresponding specifically reacting antigen to said specific antibody.

15. The method of claim 14 wherein said specific antigen is a protein, contacting is by immersing in said medium and said medium is a solution.

16. The method of claim 14 wherein said antigen is derived from a bacteria, a virus, a fungus, mammalian tissue or mammalian body fluids.

17. The method of claim 16 wherein the antibody is an immunoglobulin.

18. The method of claim 17 wherein the antibody is of the immunoglobulin IgG class.

19. A dignostic method for determining the presence or absence of a specific antibody in a biological sample comprising the steps of:
   coating a metal film onto a substrate material;
   contacting said substrate material with an aqueous medium containing a corresponding specifically reacting antigen to said specific antibody to coat all or part of said substrate material with a monomolecular layer of said specifically reacting antigen;
   immersing said coated substrate material in said sample;
   placing a mercury drop on the upper surface of said layer on said substrate material; and
   measuring the electrical capacitance between said mercury drop and said metal coating.

20. The method of claim 19 wherein the antigen is a protein, contacting is by immersing in said medium and said medium is a solution.

21. A diagnostic method for determining the presence or absence of a specific antibody in a biological sample comprising the steps of:
   coating a metal film onto a substrate material, said metal being capable of forming a visible amalgam with mercury;
   contacting said substrate material with an aqueous medium containing a corresponding specifically reacting antigen to said specific antibody to coat all or part of said substrate material with a monomolecular layer of said specifically reacting antigen;
   immersing said coated substrate material in said sample;
   placing a mercury drop on the upper surface of said layer on said substrate material; and
   measuring the time elapsing between said placing of a mercury drop and the appearance of a visible amalgam.

22. The method of claim 21 wherein the antigen is a protein, contacting is by immersing in said medium and said medium is a solution.

23. A diagnostic method for determining the presence or absence of a specific antibody in a biological sample comprising the steps of:
   coating a metal film onto a substrate material;
   contacting said substrate material with an aqueous medium containing a corresponding specifically reacting antigen to said specific antibody to coat all or part of said substrate material with a monomolecular layer of said specifically reacting antigen;
   immersing said coated substrate material in said sample;
   coating a second metal layer onto the upper surface of said layer on said substrate material; and
   viewing said substrate by reflected light.

24. The method of claim 23 wherein said coating of a second metal layer comprises electroplating said second metal layer onto said antigen layer.

25. The method of claim 23 wherein the antigen is a protein, contacting is by immersing in said medium and said medium is a solution.

26. A diagnostic method for determining the presence or absence of a specific antibody in a biological sample comprising the steps of:
   depositing indium as metal globules onto a light transmissive substrate material by evaporation from a tantalum boat at a vacuum of approximately $5 \times 10^{-5}$ mm of mercury;
   contacting said substrate material with an aqueous medium containing a corresponding specifically reacting antigen to said specific antibody to coat all or part of said substrate material with a monomolecular layer of said specifically reacting antigen;
   immersing said coated substrate material in said sample; and
   examining said coated substrate material to determine whether said substrate has a bimolecular or monomolecular layer adhering thereto.

27. The method of claim 26 wherein said antigen is a protein, contacting is by immersing in said medium and said medium is a solution.

28. A diagnostic method for determining the presence or absence of a specific antibody in a biological sample comprising the steps of:
   evaporating a metal having high atomic mobility and poor surface wetting characteristics as metal globules onto a light transmissive substrate material;
   contacting said substrate material with an aqueous medium containing a corresponding specifically reacting antigen to said specific antibody to coat all or part of said substrate material with a monomolecular layer of said specifically reacting antigen;
   immersing said coated substrate material in said sample;
   placing said substrate material, oriented with said metal and said layer downwards, onto a surface of a light reflecting liquid; and
   examining said substrate to determine whether said substrate has a bimolecular or monomolecular layer adhering thereto.

29. The method of claim 28 wherein said antigen is a protein, contacting is by immersing in said medium and said medium is a solution.

30. A diagnostic method for determining the presence or absence of a specific antibody in a biological sample comprising the steps of:
contacting a substrate material with an aqueous medium containing a corresponding specifically reacting antigen to said specific antibody to coat all or part of said substrate material with a monomolecular layer of said specifically reacting antigen;
immersing said coated substrate material in said sample; and
immersing said substrate material in an immunological bond-cleaving reagent while observing said substrate in an ellipsometer.

31. The method of claim 30 wherein said antigen is a protein, contacting is by immersing in said medium, said medium is a solution and said substrate has a surface of a material having a refractive index substantially different from the refractive index of said antibody.

32. A diagnostic method for determining the presence or absence of a specific antibody in a biological sample comprising the steps of:
contacting a substrate material having a metallic surface with an aqueous medium containing a corresponding specifically reacting antigen to said specific protein;
immersing the resulting substrate material in said sample; and
examining said substrate with electrical capacitance sensing means to determine whether said substrate has a bimolecular or monomolecular layer adhering thereto.

33. The method of claim 32 wherein said antigen is a protein, contacting is by immersing in said medium and said medium is a solution.

34. A diagnostic method for determining the presence or absence of a specific antibody in a biological sample comprising the steps of:
contacting a substrate material having a metallic surface with an aqueous medium containing a corresponding specifically reacting antigen to said specific antibody to coat all or part of said substrate with a monomolecular layer of said specifically reacting antigen, said metallic surface comprising a first electrode;
immersing the resulting substrate material in said sample;
placing a second electrode on the upper surface of said layer; and
measuring the electrical capacitance between said first and second electrodes.

35. The method of claim 34 wherein said antigen is a protein, contacting is by immersing in said medium, said medium is a solution and placing a second electrode comprises placing a mercury drop on the upper surface of said layer.

36. A diagnostic method for determining the presence or absence of a specific antibody in a biological sample comprising the steps of:
contacting a substrate material having a metallic surface with an aqueous medium containing a corresponding specifically reacting antigen to said specific antibody to coat all or part of said substrate with a monomolecular layer of said specifically reacting antigen;
immersing the resulting substrate material in said sample; and
examining said substrate employing a chemical sensing means to determine whether said substrate has a bimolecular or monomolecular layer adhering thereto.

37. The method of claim 36 wherein said antigen is a protein, contacting is by immersing in said medium, said medium is a solution, said metallic surface comprises a metal which forms a visible amalgam with mercury and said examining step further comprises the steps of:
placing a mercury drop on the upper surface of said layer; and
measuring the time elapsing between the placing of a mercury drop and the appearance of a visible amalgam.

38. The method of claim 36 wherein said examining step comprises immersing said substrate material in a weak acid solution to sever immunological bonds in said layer while observing said substrate in an ellipsometer.

39. A surface immunological test method for antibodies to hepatitis comprising exposing a slide like, metallized substrate having a monomolecular surface layer comprising hepatitis-associated antigen over all or part thereof to a solution of an antibody specific to the hepatitis-associated antigen and producing an immunological reaction therewith to form a bimolecular layer on the substrate which can be seen when the substrate is visually examined.

40. A surface immunological test method for antigens to hepatitis comprising exposing a slide like, metallized substrate having a monomolecular surface layer comprising antibody to hepatitis-associated antigens over all or part thereof to a solution of hepatitis-associated antigen and producing an immunological reaction therewith to form a bimolecular layer on the substrate which can be seen when the substrate is visually examined.

41. A surface immunological test method for gonorrhea comprising exposing a slide like, metallized substrate having a monomolecular surface layer comprising Neisseria gonorrhea antigen to a solution of an antibody specific to the Neisseria gonorrhea antigen and producing an immunological reaction therewith to form a bimolecular layer on the substrate which can be seen when the substrate is visually examined.

42. The method of claim 41 wherein said substrate is a metallized slide which also includes a metal oxide layer intermediate the metal of the slide and said monomolecular layer.

43. The method of claim 42 wherein said metal is titanium and said metal oxide is an oxide of titanium.

44. Medical diagnostic apparatus comprising:
a substrate member;
a plurality of metal globules attached to a surface of said substrate member; and
a monomolecular layer of a immunologically reactive composition overlying at least a portion of said substrate and said metal globules.

45. The apparatus of claim 44 having a plurality of said monomolecular layers, each said monomolecular layer overlying a corresponding said portion of said substrate and said metal globules.

46. The apparatus of claim 44 wherein:
said substrate member comprises a light transmissive wafer; and
said metal globules are indium particles having major dimensions in the range of 10 A to 2000 A.

47. The apparatus of claim 44 wherein the immunologically composition is an antibody.

48. The apparatus of claim 44 wherein the immunologically reactive composition is an antigen.

49. The apparatus of claim 48 wherein said antigen is a protein.

50. Medical diagnostic apparatus for detecting the presence of an antibody of interest in a fluid consisting of:
a substrate having a surface including metal; and
a monomolecular layer of a corresponding specifically reacting antigen to said antibody of interest attached to said surface.

51. Apparatus in accordance with claim 50 wherein said surface comprises gold, tantalum, indium, titanium or titanium overcoated with a layer of an oxide of titanium.

52. Apparatus for diagnosing pregnancy in accordance with claim 50 wherein.
said antigen of interest is HCG antigen;
said fluid is urine; and
said specifically reacting antibody is the specifically reacting antibody for HCG protein.

53. Apparatus for diagnosing hepatitis in accordance with claim 50 wherein:
said antibody of interest is hepatitis antibody;
said fluid is a mixture of blood and hepatitis antibody; and
said specifically reacting antigen is hepatitis-associated antigen.

54. Apparatus for diagnosing hepatitis in accordance with claim 50 wherein:
said antigen of interest is hepatitis-associated antigen;
said fluid is blood; and
said specifically reacting antibody is hepatitis antibody.

55. Apparatus in accordance with claim 50 wherein said antigen is a protein, said surface comprises gold and another metal for improving the adhesion between said gold and said substrate.

56. Apparatus in accordance with claim 55 wherein said other metal diffuses into said gold to form an alloy thereby increasing the sensitivity of said apparatus.

57. Apparatus as claimed in claim 50 wherein said surface comprises a plurality of metal globules attached to said substrate.

58. The apparatus of claim 57 wherein said metal globules consist of a metal having high atomic mobility and poor surface wetting characteristics on said substrate.

59. Apparatus for diagnosing gonorrhea in accordance with claim 50 wherein:
said antigen of interest is Neisseria gonorrhea antigen;
said fluid is blood serum; and
said specifically reacting antibody is the antibody to the Neisseria gonorrhea antigen.

60. Apparatus in accordance with claim 59 wherein said surface comprises titanium with an overlying layer comprising an oxide of titanium.

* * * * *